(12) United States Patent
Eichmann et al.

(10) Patent No.: US 11,940,398 B2
(45) Date of Patent: Mar. 26, 2024

(54) METHOD TO DETERMINE RELATIVE THERMAL MATURITY FROM POROSITIES MEASURED BY QUANTITATIVE IMAGING ON UNCLEANED SAMPLES AND GRI POROSITY MEASURED ON CRUSHED CLEANED SAMPLES

(71) Applicant: ARAMCO SERVICES COMPANY, Houston, TX (US)

(72) Inventors: Shannon Lee Eichmann, Katy, TX (US); David Jacobi, Spring, TX (US); Poorna Srinivasan, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 97 days.

(21) Appl. No.: 17/821,108

(22) Filed: Aug. 19, 2022

(65) Prior Publication Data

US 2024/0060915 A1    Feb. 22, 2024

(51) Int. Cl.
*E21B 41/00*    (2006.01)
*E21B 44/00*    (2006.01)
(Continued)

(52) U.S. Cl.
CPC ......... *G01N 23/2251* (2013.01); *E21B 41/00* (2013.01); *E21B 44/00* (2013.01);
(Continued)

(58) Field of Classification Search
CPC ............... G01N 23/2251; G01N 33/24; G01N 2223/418; G01N 2223/616; E21B 41/00;
(Continued)

(56) References Cited

U.S. PATENT DOCUMENTS 9,029,156 B2    5/2015    Kornacki et al.
10,012,764 B2   7/2018    Barwise et al.
(Continued)

FOREIGN PATENT DOCUMENTS

| AU | 2015256157 B2 | 5/2018 |
| CN | 111738978 A | 10/2020 |
| EP | 3414566 B1 | 12/2020 |

OTHER PUBLICATIONS

A. S. Sinha; "Surface Area Study in Organic-Rich Shales Using Nitrogen Adsorption", Masters Thesis; University of Oklahoma Graduate College; 2017 (144 pages).
(Continued)

*Primary Examiner* — Steven A Maconald
(74) *Attorney, Agent, or Firm* — Osha Bergman Watanabe & Burton LLP

(57) ABSTRACT

A method of determining a thermal maturity model of a subterranean region of interest is disclosed. The method includes obtaining a plurality of rock samples for the subterranean region of interest. The method further includes determining a first porosity value, a second porosity value, and a volume fraction of organic matter, for each of the plurality of rock samples. The method further includes determining, for each of the plurality of rock samples, a thermal maturity index based, at least in part, on the first porosity value, the second porosity value and the volume fraction of organic matter. The method further includes determining the thermal maturity model based, at least in part, on the thermal maturity index for each of the plurality of rock samples.

20 Claims, 9 Drawing Sheets

(51) Int. Cl.
*E21B 49/02* (2006.01)
*G01N 23/2251* (2018.01)
*G01N 33/24* (2006.01)

(52) U.S. Cl.
CPC ............ *E21B 49/02* (2013.01); *G01N 33/24* (2013.01); *E21B 2200/20* (2020.05); *E21B 2200/22* (2020.05); *G01N 2223/418* (2013.01); *G01N 2223/616* (2013.01)

(58) Field of Classification Search
CPC ...... E21B 44/00; E21B 49/02; E21B 2200/20; E21B 2200/22
See application file for complete search history.

(56) References Cited

U.S. PATENT DOCUMENTS

| | | | |
|---|---|---|---|
| 10,198,804 | B2 | 2/2019 | Sungkorn et al. |
| 10,436,865 | B2 | 10/2019 | Washburn |
| 10,900,915 | B2 | 1/2021 | Gawankar et al. |
| 11,313,224 | B2* | 4/2022 | Hakami ................ E21B 49/02 |
| 11,519,266 | B2* | 12/2022 | Kadayam Viswanathan .............. E21B 49/005 |
| 11,549,894 | B2* | 1/2023 | Soua .................... E21B 49/00 |
| 11,834,947 | B2* | 12/2023 | Ou ........................ E21B 49/00 |
| 2014/0365409 | A1* | 12/2014 | Burch ................... E21B 43/00 706/12 |
| 2017/0074772 | A1* | 3/2017 | Walls .................. G01N 15/088 |
| 2017/0226851 | A1* | 8/2017 | Hakami ............. G01N 33/2823 |
| 2017/0329045 | A1* | 11/2017 | Myers ................. G01B 11/303 |
| 2019/0227087 | A1* | 7/2019 | Belani .................... G01N 33/24 |
| 2020/0325758 | A1* | 10/2020 | Hull ........................ E21C 41/16 |
| 2020/0408090 | A1* | 12/2020 | Kadayam Viswanathan .............. E21B 49/02 |

OTHER PUBLICATIONS

D.L. Luffel and F.K. Guidry; "New Core Analysis Methods for Measuring Reservoir Rock Properties of Devonian Shale", SPE-20571-PA; Jouranl of Petroleum Technology; vol. 44; Issue 11; Nov. 1, 1992; pp. 1184-1190 (7 pages).

M. Saidian et al.; "A Comparison of Measurement Techniques for Porosity and Pore Size Distribution in Shales (mudrocks): a Case Study of Haynesville, Niobrara, Monterey and Eastern European Silurian Formations", AAPG Memoir; vol. 112; 2015 (59 pages).

B. Ma et al.; "Multiple Approaches to Quantifying the Effective Porosity of Lacustrine Shale Oil Reservoirs in Bohai Bay Basin, East China", Geofluids; vol. 2020; Aug. 25, 2020; pp. 1-13 (13 pages).

F. Chen et al.; "Total Porosity Measured for Shale Gas Reservoir Samples: A Case from the Lower Silurian Longmaxi Formation in Southeast Chongqing, China", Minerals 2019; vol. 9; No. 5; Dec. 22, 2018; pp. 1-12 (12 pages).

"Development of Laboratory and Petrophysical Techniques for Evaluating Shale Reservoirs, Final Report", GRI-95/0496; ResTech Houston Inc.; Gas Research Institute; Apr. 1996; pp. 1-304 (304 pages).

* cited by examiner

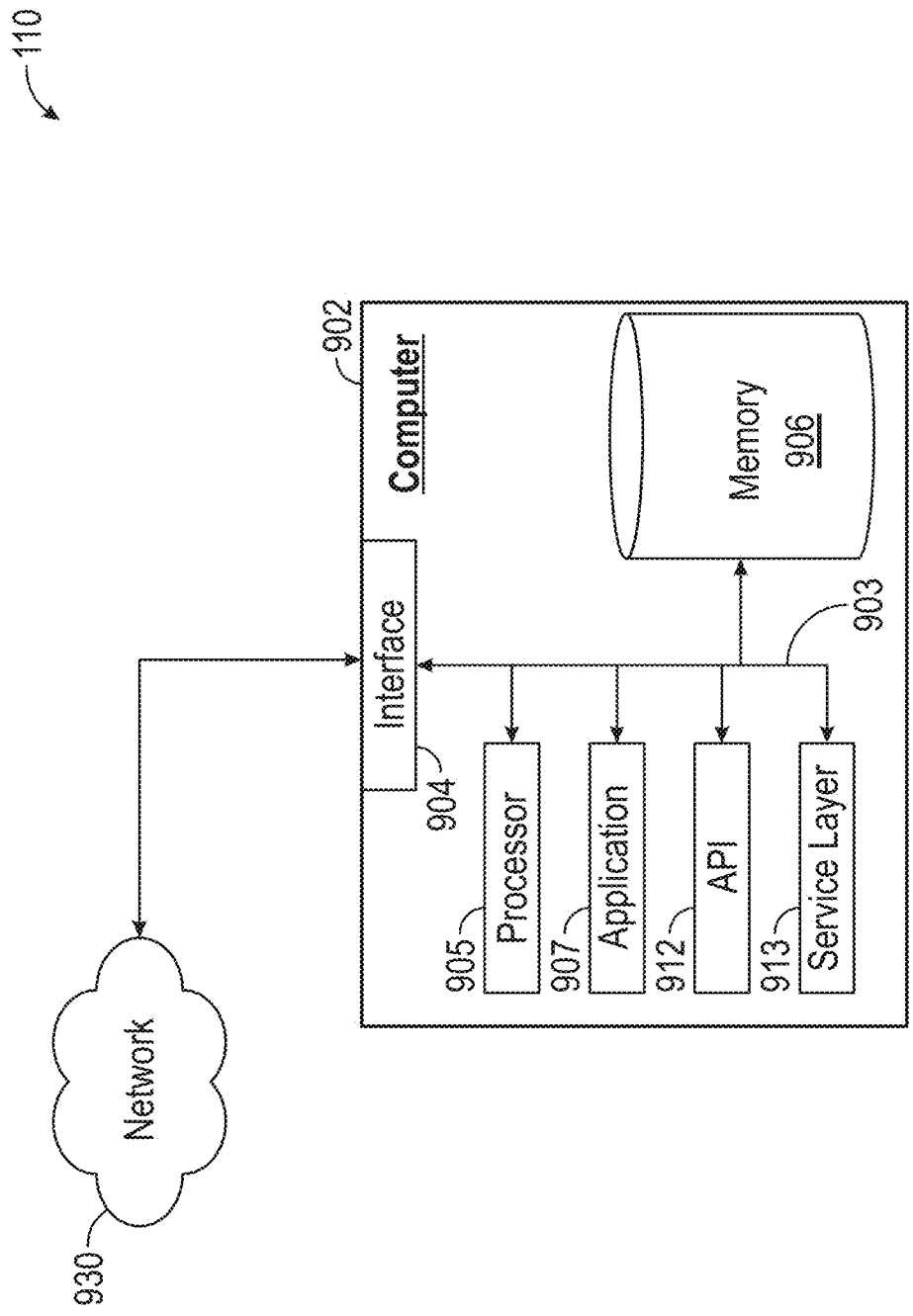

METHOD TO DETERMINE RELATIVE THERMAL MATURITY FROM POROSITIES MEASURED BY QUANTITATIVE IMAGING ON UNCLEANED SAMPLES AND GRI POROSITY MEASURED ON CRUSHED CLEANED SAMPLES

BACKGROUND

Porosity and thermal maturity of a rock formation are important properties that may be used to characterize potential hydrocarbon source rocks and hydrocarbon reservoirs. Porosity refers to void space within rock that may contain fluids, including hydrocarbons. Thermal maturity refers to the degree of thermal alteration of a hydrocarbon source rock and may be used to categorize the ability of hydrocarbon source rocks to generate hydrocarbons. The degree of thermal maturity observed in hydrocarbon source rocks may also affect porosity. Different measurement techniques for measuring porosity and thermal maturity may exhibit inconsistent results when performed on identical rock samples due to differences in preparation and measurement procedure, combined with inherent nanoscale heterogeneity of hydrocarbon source rocks. Consequently, it is desirable to develop a measure of thermal maturity that accounts for differences in measured porosities to effectively target hydrocarbons in a subterranean region of interest.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method of determining a thermal maturity model of a subterranean region of interest. The method includes obtaining a plurality of rock samples for the subterranean region of interest. The method further includes determining, for each of the plurality of rock samples, a first porosity value, determining a second porosity value, and determining an amount of organic matter. The method further includes determining, for each of the plurality of rock samples, a thermal maturity index based, at least in part, on the first porosity value, the second porosity value, and the amount of organic matter.

In general, in one aspect, embodiments relate to a non-transitory computer readable medium storing instructions executable by a computer processor. The instructions include functionality for receiving, for each of a plurality of rock samples, a bulk density, a grain density, a fluid density, and a scanning electron microscope (SEM) image of a cross section. The instructions further include functionality for determining a first porosity value based, at least in part on, the bulk density, grain density, and fluid density. The instructions further include functionality for determining a second porosity value from the SEM image, determining an amount of organic matter from the SEM image, and determining a thermal maturity index based, at least in part, on the first porosity value, the second porosity value, and the amount of organic matter. The method further includes determining a thermal maturity model based, at least in part, on the thermal maturity index for each of the plurality of rock samples.

In general, in one aspect, embodiments relate to a system including a scanning electron microscopy (SEM) configured to form an SEM image of a cross-section through a plurality of rock samples, and a computer processor. The computer processor is configured to receive, for each of the plurality of rock samples, a bulk density and a grain density, and determine a first porosity value based, at least in part, on the bulk density and the grain density. The computer processor is further configured to determine, for each of the plurality of rock samples, a second porosity value, and an amount of organic matter from the SEM image. The computer processor is further configured to determine, for each of the plurality of rock samples, a thermal maturity index based, at least in part, on the first porosity value, the second porosity value, and the amount of organic matter. The computer processor is further configured to determine a thermal maturity model based, at least in part, on the thermal maturity index for each of the plurality of rock samples.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIG. 9 depicts a computer system in accordance with one or more embodiments.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In unconventional hydrocarbon reservoirs, such as shales, tight sands, and mudrocks, pores and rock texture typically have significant spatial heterogeneity. Such heterogeneity poses challenges in measuring the petrophysical properties of these hydrocarbon source rocks and interpreting data with reference to the changing rock structure. Porosity may be measured using techniques such as the Gas Research Institute (GRI) method, two-dimensional scanning electron microscopy (2D SEM), and three-dimensional focused ion beam scanning electron microscopy (3D FIB-SEM). Solvents used for processing rock samples via the GRI method may damage the rock, causing porosity measured by the GRI method to differ from porosity measured by SEM methods. When considering thermal maturity, values may be determined using pyrolysis. Although pyrolysis is a valuable technique, factors such as contamination from oil-based mud and oxidation may affect pyrolysis data. Kerogen type and mineralogy may also influence the resultant pyrolysis values. Such challenges in measuring both porosity and thermal maturity may result in inconsistent data when studying hydrocarbon source rocks.

Figure 1:
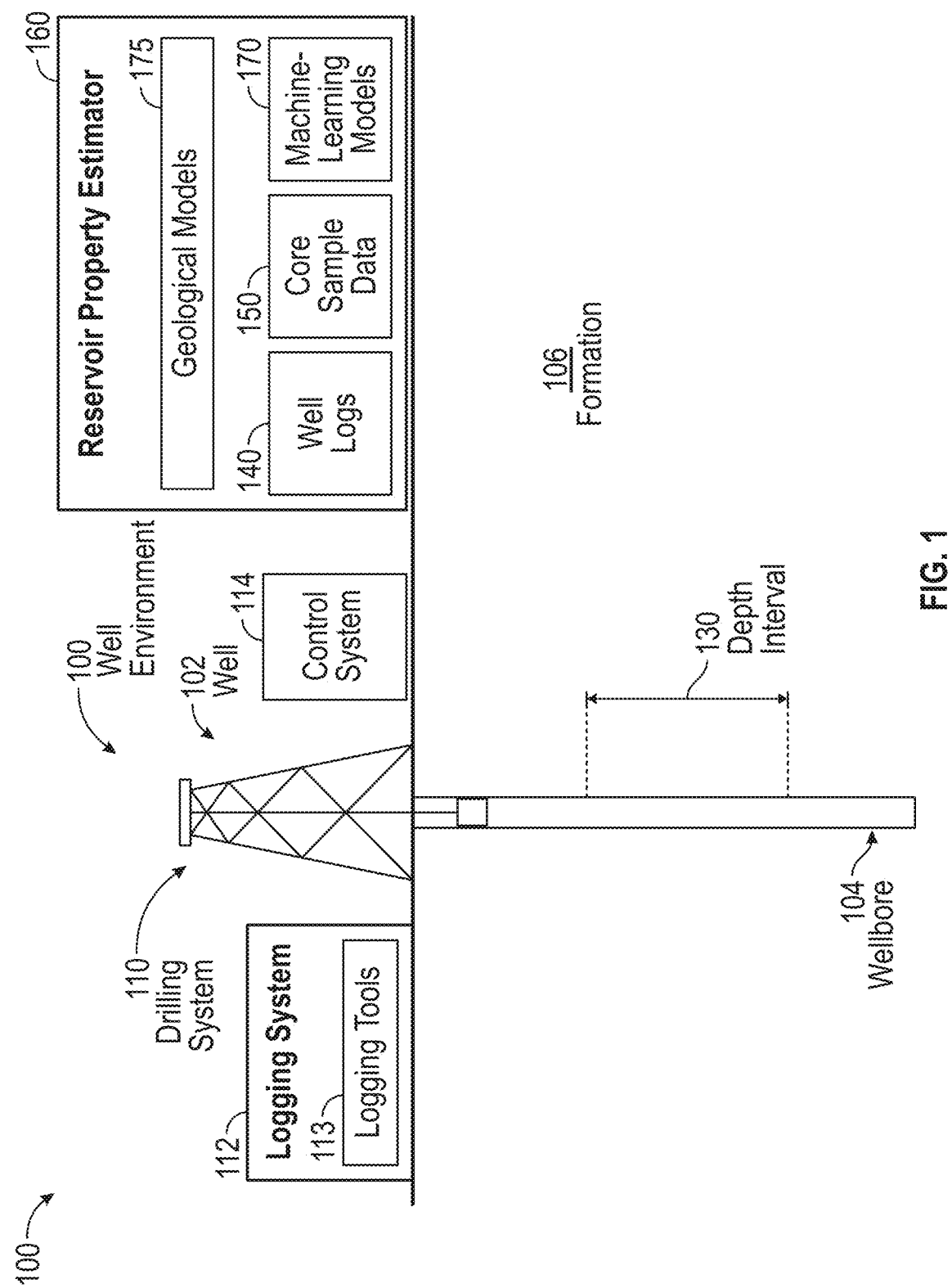
FIG. 1 depicts a well environment in accordance with one or more embodiments.

FIG. 1 illustrates a well environment (100) in accordance with one or more embodiments. The well environment (100) may include a well (102) having a wellbore (104) extending into a formation (106). The wellbore (104) may include a bored hole that extends from the surface into a target zone of the formation (106), such as a reservoir. The formation (106) may include various formation characteristics of interest, such as formation porosity, formation permeability, resistivity, density, water saturation, total organic content, volume of kerogen, Young's modulus, Poisson's ratio and the like. Porosity may indicate how much space exists in a particular rock within an area of interest in the formation (106), where oil, gas, and/or water may be trapped. Permeability may indicate the ability of liquids and gases to flow through the rock within the area of interest. Resistivity may indicate how strongly rock and/or fluid within the formation (106) opposes the flow of electrical current. For example, resistivity may be indicative of the porosity of the formation (106) and the presence of hydrocarbons. More specifically, resistivity may be relatively low for a formation that has high porosity and a large amount of water, and resistivity may be relatively high for a formation that has low porosity or includes a large volume of hydrocarbons. Water saturation may indicate the fraction of water in a given pore space.

In accordance with one or more embodiments, the well environment (100) may include a drilling system (110), a logging system (112), a control system (114), and a reservoir property estimator (160). The drilling system (110) may include a drill string, drill bit, a mud circulation system and/or the like for use in boring the wellbore (104) into the formation (106). The control system (114) may include hardware and/or software for managing drilling operations and/or maintenance operations. For example, the control system (114) may include one or more programmable logic controllers (PLCs) that include hardware and/or software with functionality to control one or more processes performed by the drilling system (110). Specifically, a programmable logic controller may control valve states, fluid levels, pipe pressures, warning alarms, and/or pressure releases throughout a drilling rig. In particular, a programmable logic controller may be a ruggedized computer system with functionality to withstand vibrations, extreme temperatures, wet conditions, and/or dusty conditions, for example, around a drilling rig. Without loss of generality, the term "control system" may refer to a drilling operation control system that is used to operate and control the equipment, a drilling data acquisition and monitoring system that is used to acquire drilling process and equipment data and to monitor the operation of the drilling process, or a drilling interpretation software system that is used to analyze and understand drilling events and progress.

In accordance with one or more embodiments, a reservoir property estimator (160) may include hardware and/or software with functionality for storing and analyzing well logs (140), core sample data (150), seismic data, and/or other types of data to generate and/or update one or more geological models (175) or machine learning models (170). Geological models may include geochemical or geomechanical models that describe structural relationships within a particular geological region. While the reservoir property estimator (160) is shown at a well site, in some embodiments, the reservoir property estimator (160) may be remote from a well site. In some embodiments, the reservoir property estimator (160) is implemented as part of a software platform for the control system (114). The software platform may obtain data acquired by the drilling system (110) and logging system (112) as inputs, which may include multiple data types from multiple sources. The software platform may aggregate the data from these systems (110, 112) in real time for rapid analysis. In some embodiments, the control system (114), the logging system (112), and/or the reservoir property estimator (160) may include a computer system that is similar to the computer system (902) described below with regard to FIG. 9 and the accompanying description.

The logging system (112) may include one or more logging tools (113), such as a nuclear magnetic resonance (NMR) logging tool and/or a resistivity logging tool, for use in generating well logs (140) of the formation (106). For example, a logging tool may be lowered into the wellbore (104) to acquire measurements as the tool traverses a depth interval (130) (e.g., a targeted reservoir section) of the wellbore (104). The plot of the logging measurements versus depth may be referred to as a "log" or "well log". Well logs (140) may provide depth measurements of the wellbore (104) that describe such reservoir characteristics as formation porosity, formation permeability, resistivity, density, water saturation, total organic content, volume of kerogen, Young's modulus, Poisson's ratio, and the like. The resulting logging measurements may be stored and/or processed, for example, by the control system (114), to generate corresponding well logs (140) for the well (102). A well log (140) may include, for example, a plot of a logging response time versus true vertical depth (TVD) across the depth interval (130) of the wellbore (104).

Reservoir characteristics may be determined using a variety of different techniques. For example, certain reservoir characteristics can be determined via coring (e.g., physical extraction of rock samples) to produce core samples and/or logging operations (e.g., wireline logging, logging-while-drilling (LWD) and measurement-while-drilling (MWD)). Coring operations may include physically extracting a rock sample from a region of interest within the wellbore (104) for detailed laboratory analysis. For example, when drilling an oil or gas well, a coring bit may cut plugs (or "cores" or "core samples") from the formation (106) and bring the plugs to the surface, and these core samples may be analyzed at the surface (e.g., in a lab) to determine various characteristics of the formation (106) at the location where the sample was obtained.

Figure 2A:
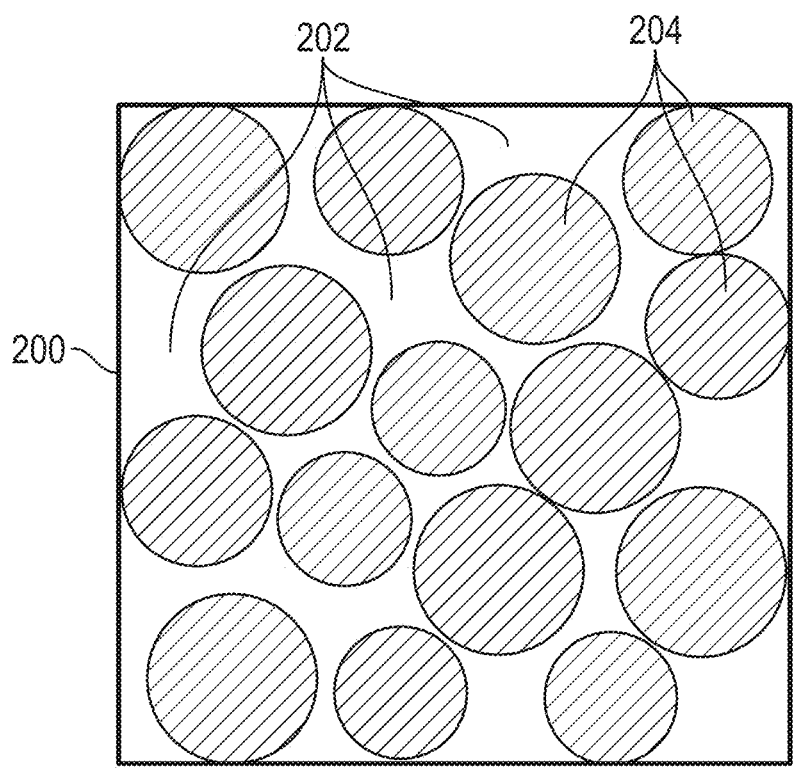
FIG. 2A depicts porosity in accordance with one or more embodiments.
Figure 2B:
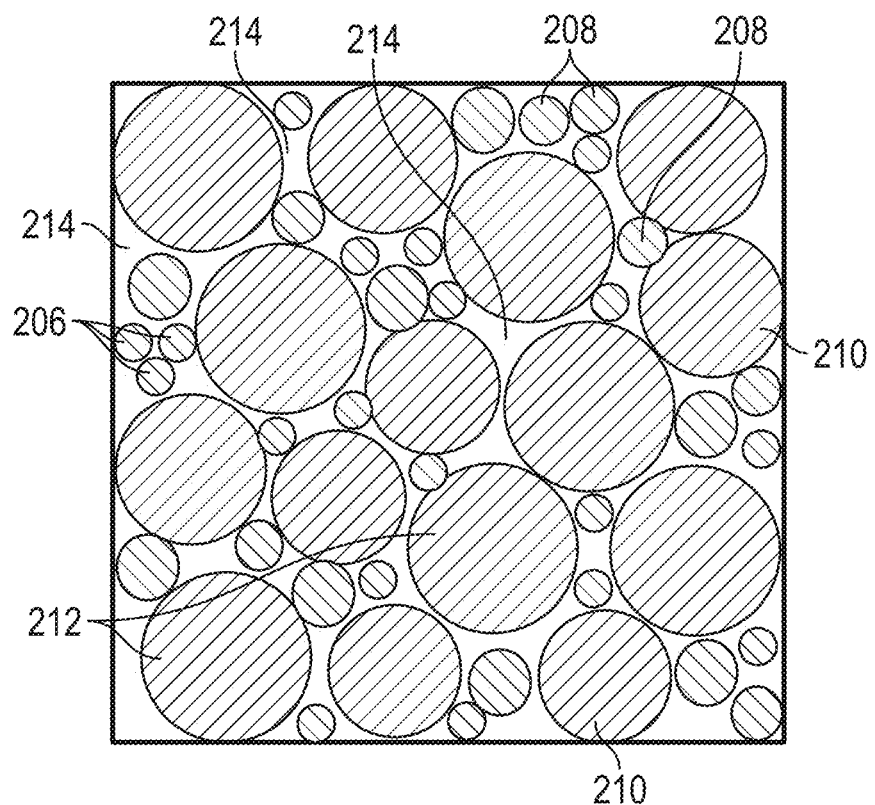
FIG. 2B depicts porosity in accordance with one or more embodiments.

FIG. 2A depicts porosity in accordance with one or more embodiments. Porosity refers to the percentage of pore (202) volume, or void space, within rock (200) that may contain fluids. Fluids may be in the form of a gas or liquid. More specifically, fluids may include oil, gas, or water. Pores (202) in typical rocks have a distribution of varying sizes. Primary porosity may form during deposition of sediment, as space develops between grains (204) of varying sizes that are not fully compacted. Secondary porosity may form through alteration of rock (200) by processes such as dolomitization, dissolution, and fracturing. Effective porosity refers to interconnected pore (202) volume in a rock (200), which may facilitate fluid flow in a hydrocarbon reservoir. Total porosity refers to total void space in the rock (200), including both isolated pores (202) and interconnected pores. Porosity, in conjunction with permeability, may be used to characterize the ability to store and transport hydrocarbons in rock (200). The depiction in FIG. 2A illustrates higher nanoscale porosity relative to the depiction in FIG. 2B. FIG. 2B is described in further detail below.

FIG. 2B depicts porosity in accordance with one or more embodiments. Specifically, FIG. 2B depicts pore (214) volume and grains of varying sizes (206, 208, 210, 212) ranging from smallest relative grain size (206) to largest relative grain size (212). As shown in FIG. 2B, the plurality of grains of varying sizes occupy additional space (208, 210) within the rock, thereby decreasing the total pore (214) volume within rock that may contain fluids, such as oil, gas, or water. The depiction in FIG. 2B illustrates lower porosity relative to the depiction in FIG. 2A.

Figure 3:
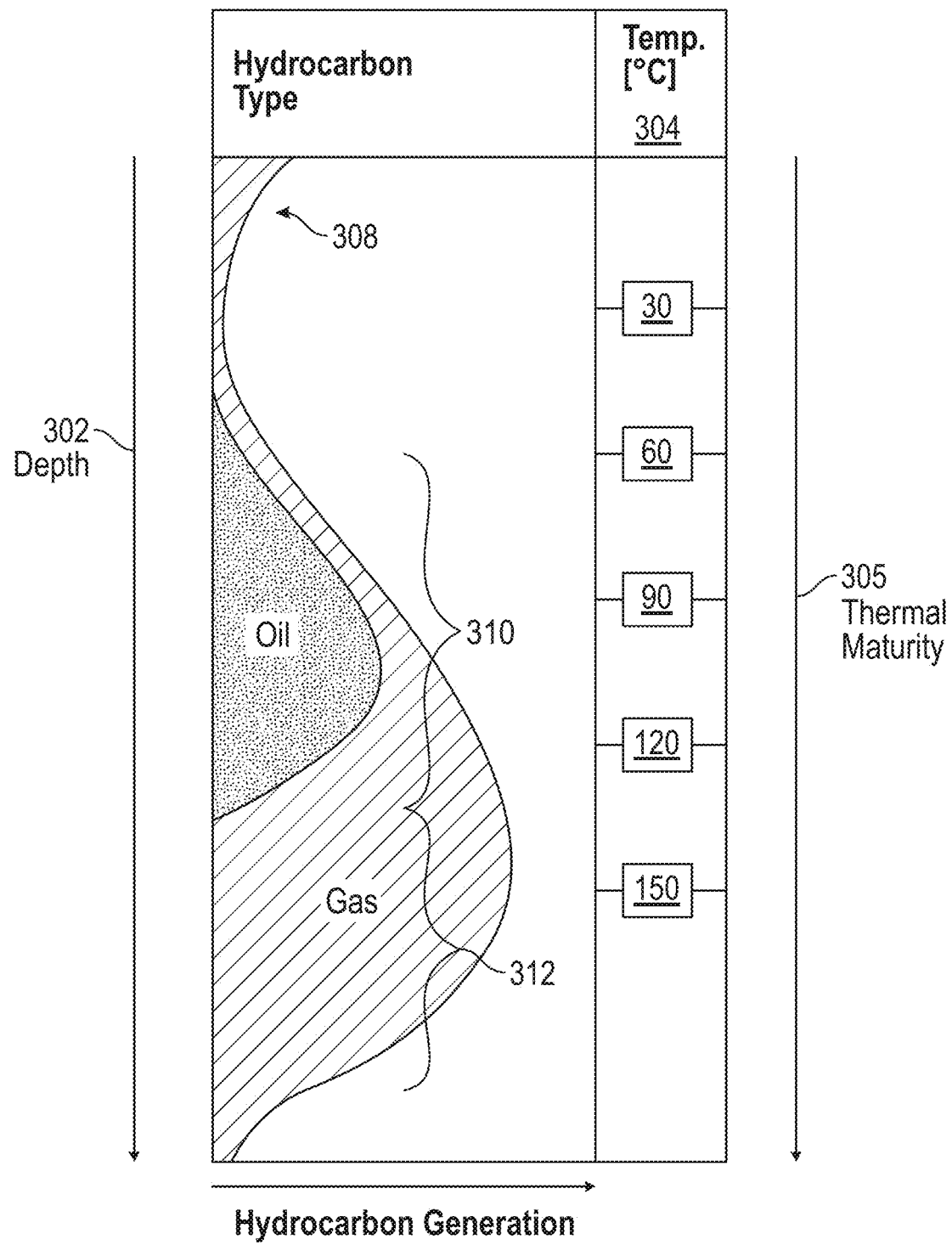
FIG. 3 depicts hydrocarbon generation in relation to depth and thermal maturity in accordance with one or more embodiments.

FIG. 3 is a graphical representation showing hydrocarbon generation in relation to depth, indicated on the left vertical axis (302), and thermal maturity, indicated on the right vertical axis (305) in accordance with one or more embodiments. Thermal maturity refers to the degree of heating of a source rock, i.e., the maximum temperature the source rock has experienced over its geological lifetime. Generally, the temperature (304) increases with depth (302); however, the relationship between depth (302) and temperature (304) may not be linear and the rate of increase may vary between geographic regions.

A source rock may be rich in organic matter. Heating a source rock may transform kerogen, or insoluble organic matter, into hydrocarbons such as oil, gas, and bitumen. Hydrocarbons may include, but are not limited to, solid and semisolid hydrocarbons. Kerogen is consumed during thermal maturation, whereas bitumen is an intermediary formed at low maturity from kerogen and consumed at higher maturities in formation of oil and gas. Thermal maturity may be used to identify and characterize prospective hydrocarbon reservoirs. Based on thermal maturity values, source rocks may be categorized in terms of their ability to generate hydrocarbons. Immature, or thermally unaltered, source rocks may generate biogenic natural gas (308). Rocks that have experienced intermediate temperatures and associated depths within a certain formation having a specific thermal gradient, may be referred to as being within the "oil window" (310). Rocks that have experienced temperatures higher temperatures and associated depths within a certain formation having a specific thermal gradient, may be referred to as being within the "gas window" (312).

In accordance with some embodiments, the temperatures provided in the following paragraphs as bounding the oil window (310) and gas window (312) should be regarded as typical values. Precise values in any given case may depend upon the type of kerogen in the source rock and the pressure to which the source rock is exposed. In accordance with some embodiments, the temperatures provided in the following paragraphs as bounding the oil window (310) and gas window (312) should be regarded as example, typical values.

Immature, or thermally unaltered, source rocks may generate biogenic natural gas (308). Processes that form biogenic natural gas (308) typically occur at lower temperatures, where organic matter may be less altered. In some cases, these temperatures may be below 50° C.

In accordance with one or more embodiments, as depth (302) and temperature (304) increase, chemical changes may generate hydrocarbons such as oil, gas, and bitumen from organic matter in the rocks. Rocks that have experienced temperatures within an intermediate range of values, for example 60° C. to 130° C. may be deemed as thermally mature rock and may generate oil. This range of temperatures, and the associated depths within a certain formation with a specific thermal gradient, may be known as the "oil window" (310). At greater depths beyond the oil window (310), rock may generate thermogenic natural gas.

Rocks that have experienced temperatures within a higher range of values, for example 130° C. to 190° C. may have generated thermogenic natural gas. This range of temperatures, and the associated depths within a certain formation with a specific thermal gradient, may be known the "gas window" (312). In the gas window (312), kerogen may be converted directly into natural gas, and oil generated earlier at lower temperatures but still within the pores may be converted into natural gas.

When temperatures exceed 200° C., beyond the initiation of the gas window (312) depth, thermal alteration may render the rock overmature, where hydrocarbon generation potential may be exhausted.

In routine core analysis, the porosity may be measured using various techniques typically on cleaned, dry rocks. Porosity methods include the Gas Research Institute method (GRI), Gas Adsorption (GA), Nuclear Magnetic Resonance (NMR), Mercury Injection Capillary Pressure (MICP), imaging with Scanning Electron Microscopy (SEM), or X-Ray Computed Tomography (CT). Each method can vary by sample size, material state (i.e., plug, crushed, or other small pieces), and preparation procedure (i.e., oven dried, cleaned, as-received, polished, etc.). In addition, some techniques measure a different property (i.e., bulk/grain density, volume of gas or mercury injected, or volumes of fluids produced) to then calculate the porosity, whereas imaging methods visualize pores for direct measurement. Typically, for source rocks, porosity may be measured using GRI, and SEM techniques.

Figure 4:
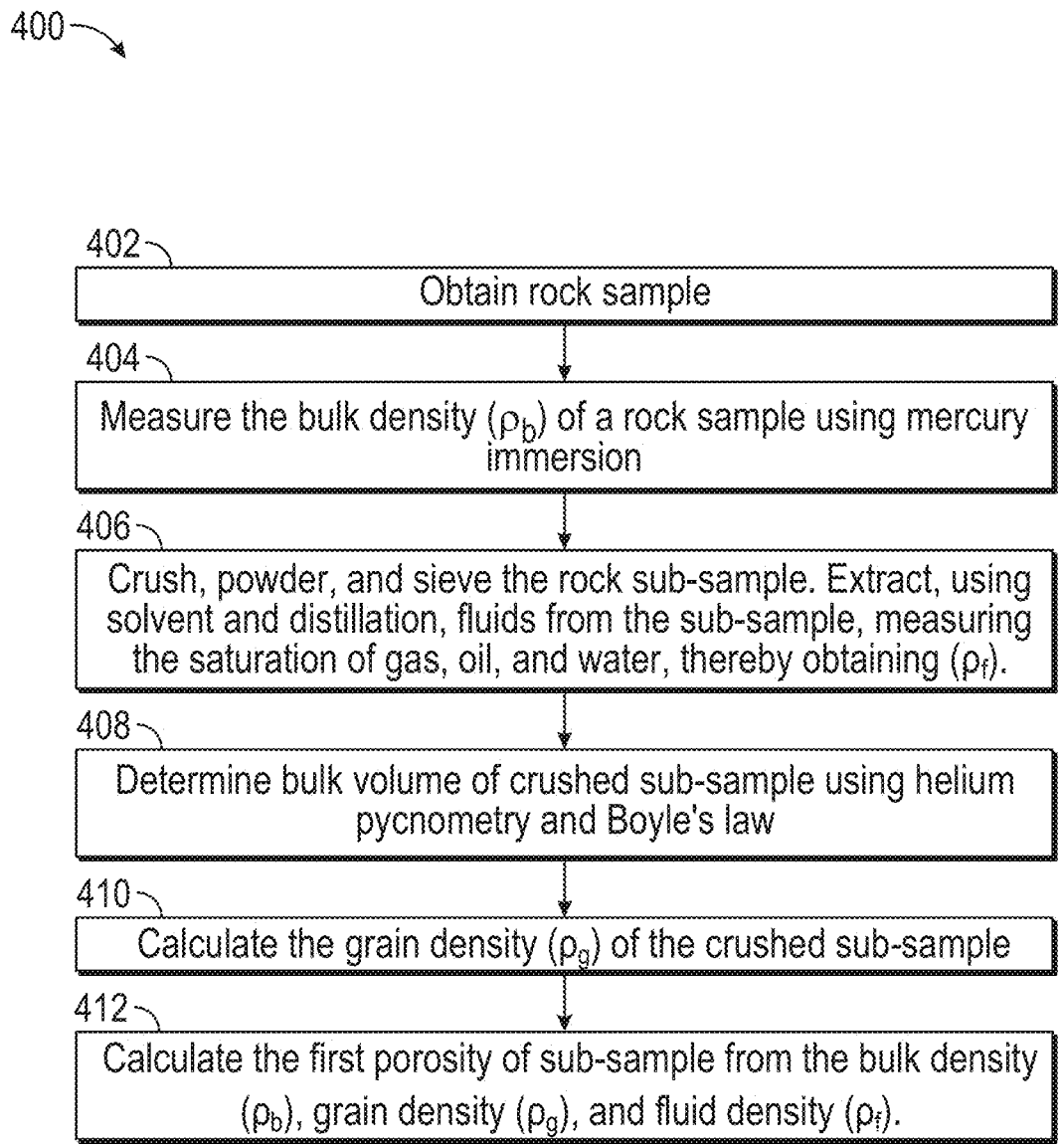
FIG. 4 shows a flowchart in accordance with one or more embodiments.

FIG. 4 shows a flowchart (400) in accordance with one or more embodiments. The flowchart (400) describes a process of obtaining porosity measurements to determine a first porosity value. The process may be a porosity determination process, familiar to a person of ordinary skill in the art, as being the process codified by the Gas Research Institute (GRI). The first porosity, $\phi GRI$, may be defined as:

$$\phi GRI = \frac{(\rho_g - \rho_b)}{(\rho_g - \rho_f)} \times 100 \qquad \text{Equation (1)}$$

where $\rho_b$ denotes bulk density of a rock sample, $\rho_g$ denotes grain density of a rock sample, and $\rho_f$ denotes pore fluid density.

In Step 402, a rock sample is obtained. The rock sample may originate from a rock core taken from a subterranean region of interest. The core may be conventionally drilled core, or "whole core" collected using a drill bit, having a circular aperture around its rotational axis. In other cases, the rock sample may be taken from a quarry or and outcrop of the rock at the surface. The rock sample may be source rock containing organic matter.

In Step 404, the bulk density ($\rho_b$) of the rock sample may be measured. In Step 404, the rock sample may be in the form of a large block of intact, uncleaned rock core. The bulk density of the rock sample may be determined using mercury immersion and Archimedes principle to measure the volume of the rock sample where the pores are filled with water and hydrocarbons. Mercury may be used because its strongly nonwetting properties, which lower the likelihood of mercury entering the pore space of the rock sample, without the application of increased pressure. Alternatively, $\rho_f$ may be determined by combining GRI measured saturations of gas, oil, and water and assumed densities for each constituent fluid.

In Step 406, a sub-sample of the rock sample may be mechanically crushed, powdered, and sieved. Further, fluids may be extracted from the sub-sample using solvents and distillation extraction, allowing the saturation of gas, oil, and water, ($\rho_f$) to be measured.

In Step 408, a volume of the crushed sub-sample obtained in Step 406 may be determined. In accordance with some embodiments, the volume of the crushed sub-sample may be measured by helium pycnometry and Boyle's law.

In Step 410, the weight of the crushed sub-sample may be determined. Further, the grain density ($\rho_g$), may then be calculated based, at least in part, on the weight and volume of the crushed sub-sample.

In Step 412, a first porosity value may be calculated based, at least in part, on the bulk density ($\rho_b$), grain density ($\rho_g$), and fluid density ($\rho_f$) The first porosity, $\phi$GRI, may be calculated using Equation (1).

Figure 6:
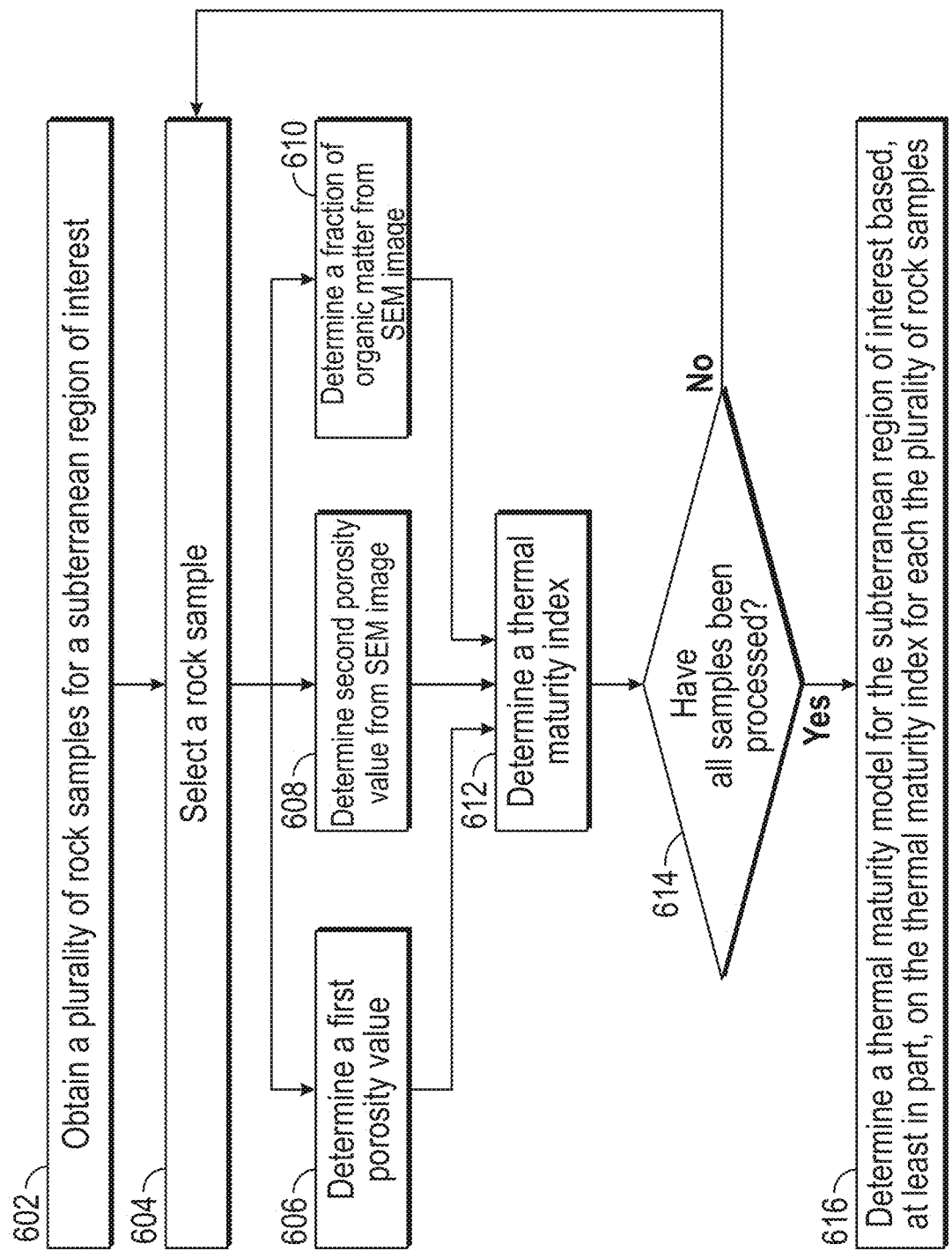
FIG. 6 shows a flowchart in accordance with one or more embodiments.

The first porosity value may be used as one input to a process for determining a thermal maturity index discussed in greater detail in FIG. 6. The first porosity value is obtained using cleaning procedures including solvents and distillation procedures on rock samples. As previously discussed, these cleaning procedures may also remove organic matter as well as hydrocarbon fluids from the rock samples. Combining the first porosity value with an alternative, second, measure of porosity that does not damage the organic matter or remove residual hydrocarbons by solvent extraction may be used to determine a thermal maturity index. A second porosity value may be obtained using SEM imaging on uncleaned rock samples, without use of solvents and cleaning procedures, in accordance with one or more embodiments.

Figure 5:
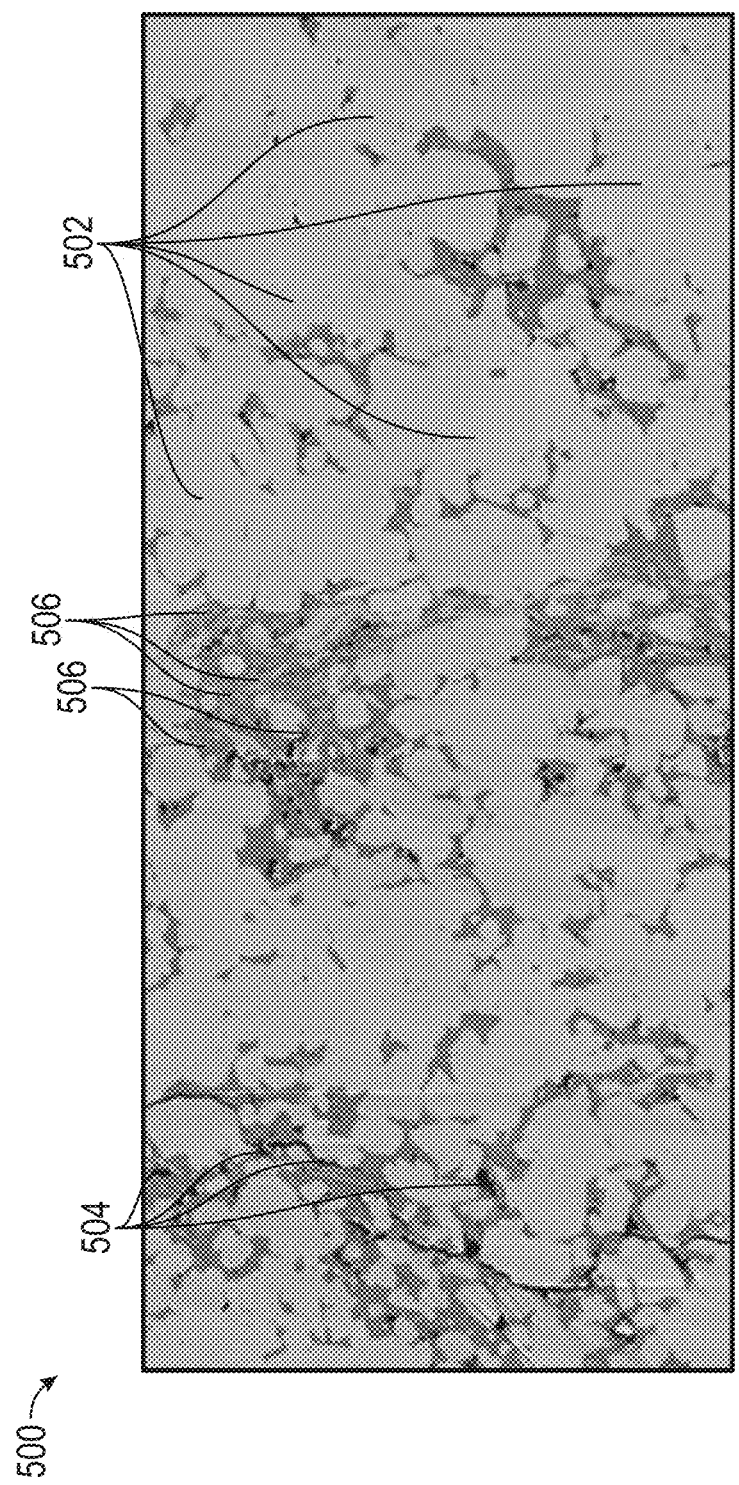
FIG. 5 shows a scanning electron microscopy (SEM) image in accordance with one or more embodiments.

FIG. 5 shows a segmented SEM image (500) displaying matrix minerals (502), pores (504), and organic matter (506). Specifically, FIG. 5 shows a segmented SEM image (500) of a cross-section through an uncleaned rock in accordance with one or more embodiments. The SEM image in FIG. 5 may be used to determine a second porosity ($\phi$SEM) value for a rock sample.

When analyzing rock structures using scanning electron microscopy (SEM) imaging methods, rock sample cross-sections may first be prepared. Preparation of the rock sample surface may include mechanical polishing and ion milling to enhance nanoscale and microscale rock sample visibility. An SEM image of the prepared cross-section of the rock sample may then be formed using a scanning electron microscope (SEM). The SEM is an instrument that produces a high-resolution image by using electrons instead of light. A beam of electrons is produced at the top of the microscope by an electron gun. The electron beam follows a vertical path through the microscope, which is contained within a vacuum. The beam travels through electromagnetic fields and lenses, which focus the beam down toward the sample. Once the beam hits the prepared cross-section of the rock sample, electrons and X-rays are ejected from the sample. Detectors collect these X-rays, backscattered electrons, and secondary electrons and convert them into a final image.

The SEM image may be a two-dimensional (2D) image (500) or a three-dimensional (3D) image (not shown). 2D SEM and three-dimensional focused ion beam scanning electron microscopy (3D FIB-SEM), as previously described, are common imaging methods used to study rock structures where significant microscale and nanoscale heterogeneity exists. The mechanical polishing and ion milling processes may be used to further smooth the surface of the rock sample and enhance contrast between the various material phases. For this application, the rock samples are only exposed to water during mechanical polishing and ion milling Rock samples are not otherwise cleaned or exposed to solvents. The high resolution of SEM is required to image the nanoscale and microscale pores in source rocks which are responsible for hydrocarbon storage and flow at this scale. Single 2D SEM images at high resolution are typically small field-of-view (FOV). When needed, a series of 2D images are collected and stitched together to increase the FOV while maintaining high resolution. 3D FIB-SEM imaging collects a series of 2D small FOV images by consecutively milling layers to expose a new part of the sample surface. Each layer is imaged, and the resultant series of images are aligned to generate a 3D rock volume. Both 2D and 3D SEM images are then segmented to label the various components of the rock (i.e., pores, organics, and matrix components).

In accordance with one or more embodiments, the SEM image (500) may be segmented into a plurality of phases based on the characteristics of the pixels within the SEM image. For example, dark pixels may be assigned to one phase and light pixels may be assigned to another phase. The SEM image may be segmented using a machine learning network or algorithm, or an intensity thresholding algorithm, or any other image segmentation method familiar to a person of ordinary skill in the art, without departing from the scope of the invention. The segmented SEM image of the cross-section may include pixels identified as a pore space phase, a matrix mineral phase and an organic matter (506) phase. The percentage of each phase may be calculated as the ratio of total number of pixels assigned to each phase to the total number of pixels in the image. These segmented areas may be used to determine a porosity value ($\phi$SEM) and an organic content value (% org, SEM).

FIG. 6 shows a flowchart in accordance with one or more embodiments. The flowchart outlines a process for determining a thermal maturity model.

In Step 602, in accordance with one or more embodiments, a plurality of rock samples may be obtained for a subterranean region of interest. The plurality of rock samples may originate from a rock cores taken from one or more depths within one or more wellbores at locations within a subterranean region of interest. The rock samples may be from the end of a plug (i.e. end-trim), cuttings, or from a whole core.

In Step 604, a first rock sample may be selected. The first rock sample may be selected from a plurality of rock samples taken from subterranean area of interest that may be investigated to contain hydrocarbon accumulations. Since the thermal maturity index is calculated independently for each rock sample, the order in which the rock samples are analyzed is irrelevant. The thermal maturity indices may be combined in Step 616 to form the thermal maturity model.

In Step 606, a first porosity value may be determined based, at least in part, on the grain density, bulk density, and fluid density of the sample as described in FIG. 4 above. The first porosity may be determined using Equation 1, previously described above. In one or more embodiments, the first porosity may be determined by the Gas Research Institute (GRI) method, familiar to one of ordinary skill in the art, and denoted $\phi$GRI.

In Step 608, a second porosity value may be determined, in accordance with one or more embodiments. The second porosity value may be determined using a SEM image as shown in FIG. 5 and described above. The SEM image may be segmented to determine a second porosity, an amount of mineral grains, and an amount of organic matter. The amount may be expressed as a volume, area, fraction, percent, or portion. The SEM image may be segmented using machine learning networks such as random forest classifiers, convolutional neural networks (CNNs), and deep learning methods or an intensity thresholding algorithm, or any other image segmentation method familiar to a person of ordinary skill in the art, without departing from the scope of the invention. The second porosity value may be denoted $\phi$SEM.

In Step 610, the amount of organic matter, denoted % org, SEM, may be determined from the SEM image. The ratio of the total number of pixels categorized by the SEM image segmentation method as organic matter (506) phase to the total number of pixels in the image, may be used to calculate the amount of organic matter value for the rock sample.

In Step 612, in accordance with one or more embodiments, a thermal maturity index, denoted $f_{mat-index}$, may be determined for the rock sample based, at least in part, on the first porosity $\phi$GRI, the second porosity $\phi$SEM, and the organic content value % org, SEM, each in units of percent. The thermal maturity index, $f_{mat-index}$, may be defined as, $$f_{mat-index} = \frac{\phi GRI - \phi SEM - A}{\%org, SEM} \quad \text{Equation (2)}$$

where A represents a correction factor. In accordance with one or more embodiments, the correction factor, A, is used to account for rock samples with low organic content values, which may become increasingly brittle and subject to induced porosity during the crushing process (406), which could impact the resulting value. Rocks with higher organic content have lower correction factor values, as they may be less brittle and thereby less likely to be subjected to induced porosity during the crushing process (406).

In accordance with one or more embodiments, each rock sample may be assigned a correction factor, A, in relation to its organic content value, % org, SEM. For example, for rock samples with % org, SEM values less than 10% as determined in Step 610, A=2. For % org, SEM values between 10%, and 15% as determined in Step 610, A=1. For % org, SEM values greater than 15% as determined in Step 610, A=0.

In Step 614, if all rock samples have been processed using Step 604 through Step 610, the workflow continues to Step 616. Alternatively, in Step 614, if all rock samples have not yet been processed via Step 604-Step 610, the workflow returns to Step 604 to select a new rock sample and repeat Step 606 through Step 614 for the new rock sample.

In Step 616, in accordance with one or more embodiments, a thermal maturity model is determined for the subterranean region of interest based, at least in part, on the thermal maturity index for each of the plurality of rock samples. Step 616 is discussed in greater detail in FIG. 7 below. The subterranean region of interest may refer to a subterranean 3D volume, a 2D cross-section through the 3D volume, or a one-dimensional line through the 3D volume. As such, the subterranean region of interest may include different longitudinal and latitudinal locations, as well as different depths within the same longitudinal and latitudinal location, within a sedimentary basin. In other words, the subterranean region of interest may include a plurality of rock samples sourced across multiple regions of the sedimentary basin. The subterranean region of interest may also include a plurality of rock samples taken from multiple depths within a single well of the sedimentary basin.

Figure 7:
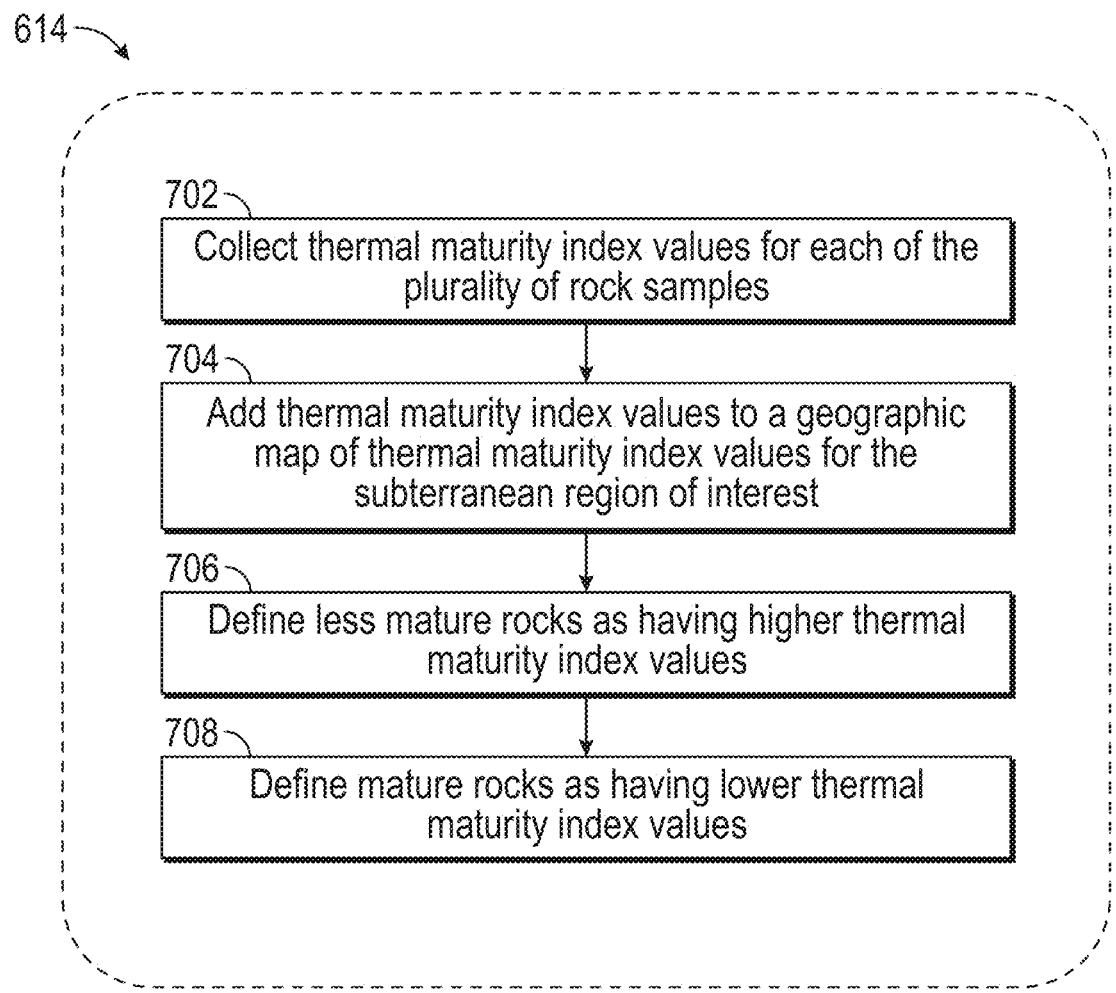
FIG. 7 shows a flowchart for determining a thermal maturity model in accordance with one or more embodiments.

FIG. 7 shows a flowchart for determining a thermal maturity model from the plurality of thermal maturity indices, in accordance with one or more embodiments. In Step 702, thermal maturity index values for each of the plurality of rock samples may be assembled.

In Step 704, in accordance with one or more embodiments, a thermal maturity model may be formed by displaying the thermal maturity index values using the spatial location at which each sample was collected, as a geographic map of thermal maturity index values for the subterranean region of interest. The map may be a two-dimensional (2D) surface, or a three-dimensional(3D) volume. Additional values for unsampled locations in the thermal maturity model may be determined using interpolation, extrapolation, smoothing, kriging, or other statistical methods of predicting unsampled values familiar to a person of ordinary skill in the art. The thermal maturity index values may be displayed using a color scale, a grayscale, and/or using contours.

In Step 706, the thermal maturity model may be interpreted, in accordance with one or more embodiments. Regions of the thermal maturity model displaying higher thermal maturity index values may be interpreted as having lesser thermal maturity. Conversely, in Step 708, regions of the thermal maturity model displaying lower thermal maturity index values may be interpreted as having greater thermal maturity.

In one or more embodiments, the thermal maturity model may be used to determine the likely location of hydrocarbons in a subterranean region of interest. The location may include the latitude, longitude and depth extents of the hydrocarbons or, in other words, the spatial extent of the reservoir in all three dimensions. These locations may in turn be used to identify drilling targets to drill a wellbore to produce the hydrocarbons to the surface. The target may include a latitude, longitude and depth at which the wellbore is planned to enter the hydrocarbon reservoir and/or terminate within the hydrocarbon reservoir.

In accordance with one or more embodiments, a drilling target may be determined based upon the thermal maturity model. In particular, one or more zones may be targeted based on the thermal maturity model determined from the plurality of thermal maturity index values. Further, a wellbore path may be planned to target these zones. For example, favorable source rocks determined using the workflow described in FIG. 6 may be further targeted with additional wells drilled from the surface or extending off from a location within an already drilled wellbore (104), such as the wellbore (104) in which the source rocks were sampled to determine the thermal maturity model. Such wells, referred to as "side-track" wells or "side-tracks" may target the portions of the formation determined to have favorable characteristics such as high porosity.

Furthermore, a wellbore planning system may be used to plan the wellbore trajectory, including the orientation and changes in diameter of the wellbore (104) along the trajectory and the angle of incidence at which the wellbore enters the target zone. The wellbore planning system may include a computer processor with hardware appropriate software to plan an optimized wellbore trajectory. The wellbore planning system may take as inputs such factors such as the available surface well locations or kick-off points, drilling target point coordinates, the maximum permissible curvature ("dog-leg, or "build-rate"), and geological and geomechanical constraints. The wellbore planning system may further incorporate limitations such as maximum torque and drag, and the mechanical strength of the drill string, casing, bottomhole assemblies, logging tools and completion strings.

Figure 8:
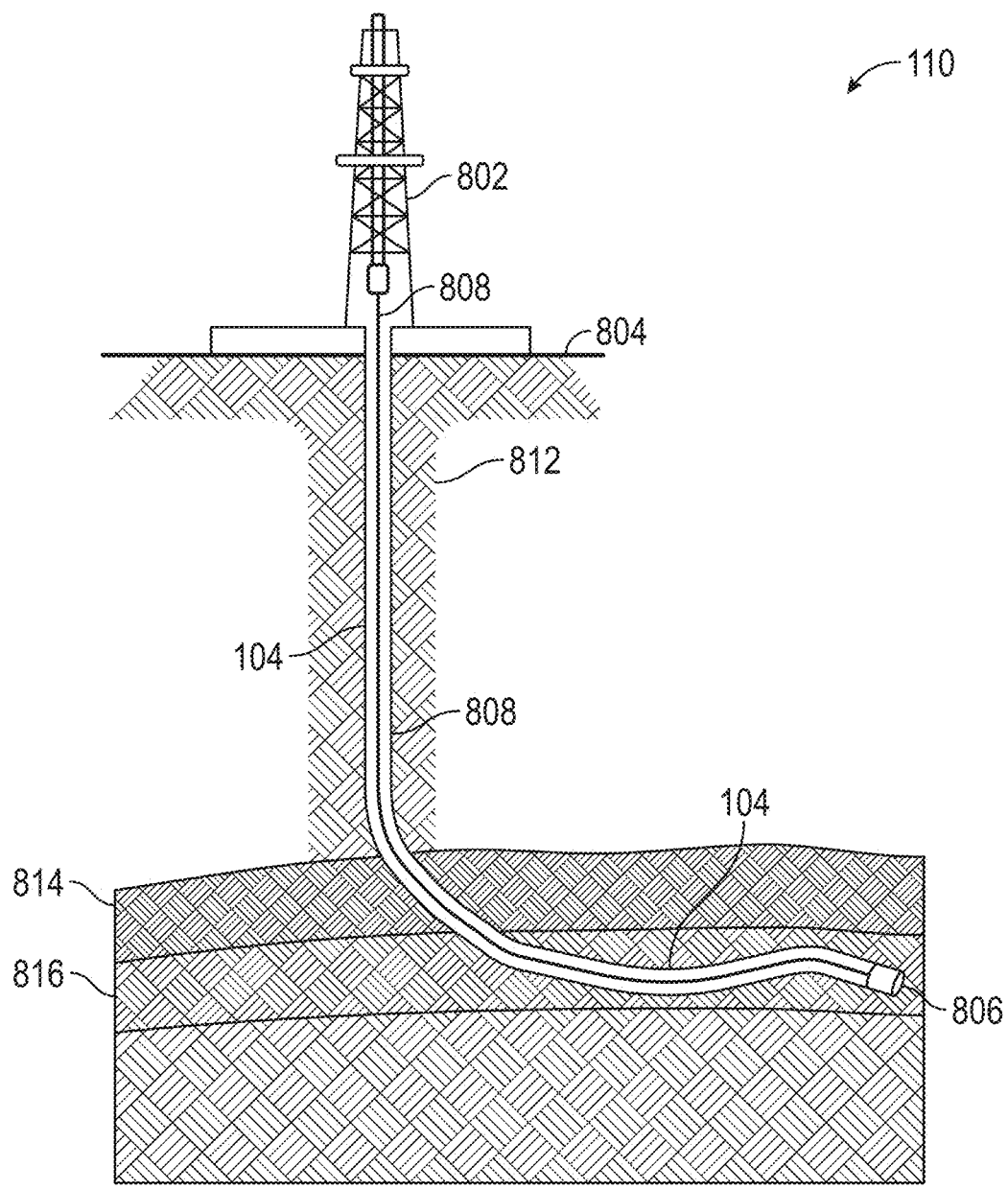
FIG. 8 depicts a drilling system in accordance with one or more embodiments.

FIG. 8 shows a drilling system (110) in accordance with one or more embodiments. The drilling system may drill a wellbore along the wellbore trajectory determined using the wellbore planning system. The drilling system (110) may include a derrick (802). In some embodiments, the derrick (802) may be located on the land surface (804). In other embodiments, the derrick may be located on a jack-up drill rig (not shown), or a floating drill rig (not shown), on a drill ship (not shown). A drill bit (806) suspended by a drill string (808) from the derrick (802) may drill a wellbore (104) through the subsurface. In accordance with one or more embodiments, the wellbore may be vertical, highly deviated or horizontal. The wellbore (104) may traverse a plurality of overburden layers (812) and one or more cap-rock layers (814). The wellbore (104) may penetrate one or more hydrocarbon reservoirs (816).

In other embodiments, completion decisions such as where and how to hydraulically fracture the formation or where to acidize the formation to enhance production may be made based, at least in part, on the reservoir evaluation obtained using the workflow described in FIG. 7. In still further embodiments, surface production facilities such as pipelines and gas-oil separation plants may be determined based upon the thermal maturity model generated using the workflows described in FIGS. 6 and 7. As a result of the workflows described in FIGS. 6 and 7, these completion and production decisions may be guided, at least in part, by the thermal maturity model, thermal maturity index, and associated values for φGRI, φSEM, and % org, SEM.

FIG. 9 further depicts a block diagram of the computer system (902) used to provide computational functionalities associated with described algorithms, methods, functions, processes, flows, and procedures as described in this disclosure, according to one or more embodiments. The illustrated computer (902) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (902) may include a computer that includes an input device, such as a keypad, keyboard, touch screen, or other device that can accept user information, and an output device that conveys information associated with the operation of the computer (902), including digital data, visual, or audio information (or a combination of information), or a Graphical User Interface (GUI).

The computer (902) can serve in a role as a client, network component, a server, a database or other persistency, or any other component (or a combination of roles) of a computer system for performing the subject matter described in the instant disclosure. The illustrated computer (902) is communicably coupled with a network (930). In some implementations, one or more components of the computer (902) may be configured to operate within environments, including cloud-computing-based, local, global, or other environment (or a combination of environments).

At a high level, the computer (902) is an electronic computing device operable to receive, transmit, process, store, or manage data and information associated with the described subject matter. According to some implementations, the computer (902) may also include or be communicably coupled with an application server, e-mail server, web server, caching server, streaming data server, business intelligence (BI) server, or other server (or a combination of servers).

The computer (902) can receive requests over network (930) from a client application (for example, executing on another computer (902) and responding to the received requests by processing the said requests in an appropriate software application. In addition, requests may also be sent to the computer (902) from internal users (for example, from a command console or by other appropriate access method), external or third-parties, other automated applications, as well as any other appropriate entities, individuals, systems, or computers.

Each of the components of the computer (902) can communicate using a system bus (903). In some implementations, any or all of the components of the computer (902), both hardware or software (or a combination of hardware and software), may interface with each other or the interface (904) (or a combination of both) over the system bus (903) using an application programming interface (API) (912) or a service layer (913) (or a combination of the API (912) and service layer (913). The API (912) may include specifications for routines, data structures, and object classes. The API (912) may be either computer-language independent or dependent and refer to a complete interface, a single function, or even a set of APIs. The service layer (913) provides software services to the computer (902) or other components (whether or not illustrated) that are communicably coupled to the computer (902). The functionality of the computer (902) may be accessible for all service consumers using this service layer. Software services, such as those provided by the service layer (913), provide reusable, defined business functionalities through a defined interface. For example, the interface may be software written in JAVA, C++, or other suitable language providing data in extensible markup language (XML) format or another suitable format. While illustrated as an integrated component of the computer (902), alternative implementations may illustrate the API (912) or the service layer (913) as stand-alone components in relation to other components of the computer (902) or other components (whether or not illustrated) that are communicably coupled to the computer (902). Moreover, any or all parts of the API (912) or the service layer (913) may be implemented as child or sub-modules of another software module, enterprise application, or hardware module without departing from the scope of this disclosure.

The computer (902) includes an interface (904). Although illustrated as a single interface (904) in FIG. 9, two or more interfaces (904) may be used according to particular needs, desires, or particular implementations of the computer (902). The interface (904) is used by the computer (902) for communicating with other systems in a distributed environment that are connected to the network (930). Generally, the interface (904) includes logic encoded in software or hardware (or a combination of software and hardware) and operable to communicate with the network (930). More specifically, the interface (904) may include software supporting one or more communication protocols associated with communications such that the network (930) or interface's hardware is operable to communicate physical signals within and outside of the illustrated computer (902).

The computer (902) includes at least one computer processor (905). Although illustrated as a single computer processor (905) in FIG. 9, two or more processors may be used according to particular needs, desires, or particular implementations of the computer (902). Generally, the computer processor (905) executes instructions and manipulates data to perform the operations of the computer (902) and any algorithms, methods, functions, processes, flows, and procedures as described in the instant disclosure.

The computer (902) also includes a memory (906) that holds data for the computer (902) or other components (or a combination of both) that can be connected to the network (930). For example, memory (906) can be a database storing data consistent with this disclosure. Although illustrated as a single memory (906) in FIG. 9, two or more memories may be used according to particular needs, desires, or particular implementations of the computer (902) and the described functionality. While memory (906) is illustrated as an integral component of the computer (902), in alternative implementations, memory (906) can be external to the computer (902).

The application (907) is an algorithmic software engine providing functionality according to particular needs, desires, or particular implementations of the computer (902), particularly with respect to functionality described in this disclosure. For example, application (907) can serve as one or more components, modules, applications, etc. Further, although illustrated as a single application (907), the application (907) may be implemented as multiple applications (907) on the computer (902). In addition, although illustrated as integral to the computer (902), in alternative implementations, the application (907) can be external to the computer (902).

There may be any number of computers (902) associated with, or external to, a computer system containing computer (902), wherein each computer (902) communicates over a network (930). Further, the term "client," "user," and other appropriate terminology may be used interchangeably as appropriate without departing from the scope of this disclosure. Moreover, this disclosure contemplates that many users may use one computer (902), or that one user may use multiple computers (902).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed is:

1. A method of determining a thermal maturity model of a subterranean region of interest, comprising:
    obtaining a plurality of rock samples for the subterranean region of interest;
    for each of the plurality of rock samples, using a computer processor:
        determining a first porosity value,
        determining a second porosity value,
        determining an amount of organic matter,
        determining a thermal maturity index based, at least in part, on the first porosity value, the second porosity value and the amount of organic matter, and
    determining, using a computer processor, the thermal maturity model based, at least in part, on the thermal maturity index for each of the plurality of rock samples.

2. The method of claim 1, further comprising planning a wellbore trajectory using a wellbore planning system based, at least in part, on the thermal maturity model.

3. The method of claim 2, further comprising drilling a wellbore based, at least in part, on the planned wellbore trajectory using a drilling system.

4. The method of claim 1, wherein determining the first porosity value comprises:
    determining a bulk density;
    determining a grain density;
    determining a fluid density, and
    determining the first porosity based, at least in part on a ratio of the bulk density to the grain density.

5. The method of claim 1, wherein determining the second porosity value comprises:
    determining a scanning electron microscope (SEM) image of a cross-section through the sample;
    segmenting the SEM image into a labeled pore space phase, and a labeled matrix mineral phase, and a labeled organic matter phase; and
    determining the second porosity value based upon a total area of labeled pore pixels and a total area of the SEM image.

6. The method of claim 5, wherein segmenting the SEM image comprises applying a trained machine learning network to the SEM image.

7. The method of claim 1, wherein determining the amount of organic matter comprises:
    determining a scanning electron microscope (SEM) image of a cross-section through the sample;
    segmenting the SEM image into a labeled pore space phase, and a labeled matrix mineral phase, and a labeled organic matter phase; and
    determining the amount of organic matter based upon a total area of labeled organic matter pixels and a total area of the SEM image.

8. The method of claim 1, wherein a low value of the thermal maturity index indicates a high thermal maturity.

9. A non-transitory computer readable medium storing instructions executable by a computer processor, the instructions comprising functionality for:
    receiving, for each of a plurality of rock samples:
        a bulk density,
        a grain density,
        a fluid density, and
        a scanning electron microscope (SEM) image of a cross-section;

determining a first porosity value based, at least in part on, the bulk density, grain density, and fluid density;

determining a second porosity value from the SEM image, determining an amount of organic matter from the SEM image, determining a thermal maturity index based, at least in part, on the first porosity value, the second porosity value and the amount of organic matter; and determining, using a computer processor, a thermal maturity model based, at least in part, on the thermal maturity index for each of the plurality of rock samples.

10. The non-transitory computer readable medium of claim 9, the instructions furthering comprising functionality for planning a wellbore trajectory based, at least in part, on the thermal maturity model.

11. The non-transitory computer readable medium of claim 9, wherein determining the first porosity is based, at least in part on a ratio of the bulk density to the grain density.

12. The non-transitory computer readable medium of claim 9, wherein determining the second porosity value comprises:

segmenting the SEM image into a labeled pore space phase, a labeled matrix mineral phase, and a labeled organic matter phase; and determining the second porosity value based upon a total area of labeled pore pixels and a total area of the SEM image.

13. The non-transitory computer readable medium of claim 12, wherein segmenting the SEM image comprises applying a trained machine learning network to the SEM image.

14. The non-transitory computer readable medium of claim 9, wherein determining the amount of organic matter comprises:

segmenting the SEM image into a labeled pore space phase, a labeled matrix mineral phase, and a labeled organic matter phase; and determining the amount of organic matter based upon a total area of labeled organic matter pixels and a total area of the SEM image.

15. A system comprising:

a scanning electron microscope (SEM) configured to form an SEM image of a cross-section through a plurality of rock samples;

a computer processor, configured to:

for each of the plurality of the rock samples, receive a bulk density and a grain density, determine a first porosity value based, at least in part, on the bulk density and the grain density, from the SEM image:

determine a second porosity value; and determine an amount of organic matter, and determine a thermal maturity index based, at least in part, on the first porosity value, the second porosity value and the amount of organic matter; and determine a thermal maturity model based, at least in part, on the thermal maturity index for each of the plurality of rock samples.

16. The system of claim 15, further comprising a wellbore planning system configured to plan a planned wellbore trajectory using a wellbore planning system based, at least in part, on the thermal maturity model.

17. The system of claim 16, further comprising wellbore drilling system configured to drill a wellbore based, at least in part, on the planned wellbore trajectory.

18. The system of claim 16, wherein determining the second porosity value comprises:

segmenting the SEM image into a labeled pore space phase, a labeled matrix mineral phase, and a labeled organic matter phase; and determining the second porosity value based upon a total area of labeled pore pixels and a total area of the SEM image.

19. The system of claim 15, wherein determining the amount of organic matter comprises:

segmenting the SEM image into a labeled pore space phase, a labeled matrix mineral phase, and a labeled organic matter phase; and determining the amount of organic matter based upon a total area of labeled organic matter pixels and a total area of the SEM image.

20. The system of claim 15, wherein segmenting the SEM image comprises applying a trained machine learning network to the SEM image.

* * * * *